(12) United States Patent
Hirokawa et al.

(10) Patent No.: US 7,101,694 B2
(45) Date of Patent: Sep. 5, 2006

(54) GENES ENCODING PROTEINS CAPABLE OF REGENERATING LUCIFERIN, RECOMBINANT DNA AND PROCESS FOR PRODUCING PROTEIN CAPABLE OF REGENERATING LUCIFERIN

(75) Inventors: Kozo Hirokawa, Chiba (JP); Keiko Kurosawa, Chiba (JP); Naoki Kajiyama, Chiba (JP)

(73) Assignee: Kikkoman Corporation, Noda (JP)

( * ) Notice: Subject to any disclaimer, the term of this patent is extended or adjusted under 35 U.S.C. 154(b) by 438 days.

(21) Appl. No.: 10/333,740

(22) PCT Filed: Jul. 26, 2001

(86) PCT No.: PCT/JP01/06455

§ 371 (c)(1),
(2), (4) Date: Jan. 28, 2003

(87) PCT Pub. No.: WO02/10384

PCT Pub. Date: Feb. 7, 2002

(65) Prior Publication Data

US 2004/0072178 A1 Apr. 15, 2004

(30) Foreign Application Priority Data

Jul. 28, 2000 (JP) ........................................ 2000-228227

(51) Int. Cl.
| | |
|---|---|
| C12P 9/02 | (2006.01) |
| C12N 15/00 | (2006.01) |
| C12N 1/20 | (2006.01) |
| C12D 21/06 | (2006.01) |
| C07H 21/04 | (2006.01) |

(52) U.S. Cl. .................. 435/189; 536/23.2; 435/320.1; 435/69.1; 435/252.3; 435/348; 435/254.2; 435/254.11; 435/252.33; 435/325; 530/350

(58) Field of Classification Search ................. 435/189, 435/320.1, 252.33, 69.1, 348, 252.3, 254.2, 435/254.11, 325; 536/23.2; 530/350
See application file for complete search history.

(56) References Cited

U.S. PATENT DOCUMENTS 5,814,504 A   9/1998 Kajiyama

FOREIGN PATENT DOCUMENTS

JP   01/25426   4/2001

OTHER PUBLICATIONS

K. Okada, et al., Tetrahedron Letters, Pergamon Press, No. 32, XP-002109172, pp. 2771–2774, "Firefly Bioluminescence III. Conversion of Oxyluciferin to Luciferin in Firefly", 1974.
K. Gomi, et al., Gene An International Journal on Genes and Genomes, ELSEVIER, vol. 294, No. 1–2, XP-004381348, pp. 157–166, "Molecular Cloning and Expression of the cDNAs Encoding Luciferinregenerating Enzyme from Luciola Cruciata and Luciola Lateralis", Jul. 10, 2002.

*Primary Examiner*—Rebecca E. Prouty
*Assistant Examiner*—Malgorzata A. Walicka
(74) *Attorney, Agent, or Firm*—Oblon, Spivak, McClelland, Maier & Neustadt, P.C.

(57) ABSTRACT

The present invention relates to:

an isolated or synthesized gene, which encodes a protein comprising the amino acid sequence represented by SEQ ID NO: 2, an isolated or synthesized gene, which encodes a protein comprising an amino acid sequence comprising a deletion, substitution or addition of one or more amino acids with respect to the amino acid sequence represented by SEQ ID NO: 2 and being capable of regenerating luciferin, an isolated or synthesized gene, which hybridizes with the complementary strand sequence of a DNA comprising the nucleotide sequence represented by SEQ ID NO: 1 under stringent conditions and encodes a protein capable of regenerating luciferin, a recombinant DNA, which is characterized in that the above-described isolated or synthesized gene is inserted into a vector DNA, a transformant or transductant comprising the above-described recombinant DNA, and a process for producing a protein capable of regenerating luciferin, which is characterized in that the method comprises culturing the above-described transformant or transductant in a medium and collecting therefrom the protein capable of regenerating luciferin.

12 Claims, No Drawings

SEQUENCE LISTING

<160> NUMBER OF SEQ ID NOS: 12

<210> SEQ ID NO 1
<211> LENGTH: 924
<212> TYPE: DNA
<213> ORGANISM: Luciola lateralis
<220> FEATURE:
<221> NAME/KEY: CDS
<222> LOCATION: (1)..(924)
<223> OTHER INFORMATION:

<400> SEQUENCE: 1

```
atg tcg cca gtt att gaa cag atc act gaa gta gac aat ttc caa atc      48
Met Ser Pro Val Ile Glu Gln Ile Thr Glu Val Asp Asn Phe Gln Ile
1               5                   10                  15 gga gag ggt cca cac tgg gat acc gaa aca caa agt ttg tat ttt gtg      96
Gly Glu Gly Pro His Trp Asp Thr Glu Thr Gln Ser Leu Tyr Phe Val
            20                  25                  30 gat att cta gaa aaa tcc ata cac aaa tac gta cca tcg aca aaa caa     144
Asp Ile Leu Glu Lys Ser Ile His Lys Tyr Val Pro Ser Thr Lys Gln
        35                  40                  45 cat act aaa atg att ttg aat aaa cgt ccg tct ttt att ata cca ata     192
His Thr Lys Met Ile Leu Asn Lys Arg Pro Ser Phe Ile Ile Pro Ile
    50                  55                  60 aaa gaa aca tct gat cgg ttt gtc ata agt tta gaa cga gac att tgc     240
Lys Glu Thr Ser Asp Arg Phe Val Ile Ser Leu Glu Arg Asp Ile Cys
65                  70                  75                  80 gtt ctt act tgg gat ggt gtt agt gcc acg cca agt cat tta gaa aca     288
Val Leu Thr Trp Asp Gly Val Ser Ala Thr Pro Ser His Leu Glu Thr
                85                  90                  95 ata gtt acc gtt gat acg gga atc gaa gga aat aca ttc aat gat ggt     336
Ile Val Thr Val Asp Thr Gly Ile Glu Gly Asn Thr Phe Asn Asp Gly
            100                 105                 110 aaa gca gat gcg ttt ggc aat ttg tgg gca ggt aca tta tat agt aaa     384
Lys Ala Asp Ala Phe Gly Asn Leu Trp Ala Gly Thr Leu Tyr Ser Lys
        115                 120                 125 ttc gat att gaa aaa caa ggt cct aat aca gga aca ttg tac agc ctg     432
Phe Asp Ile Glu Lys Gln Gly Pro Asn Thr Gly Thr Leu Tyr Ser Leu
    130                 135                 140 tct aat aag cag tta aga aaa cat att tct aat atc ttc cta tca aat     480
Ser Asn Lys Gln Leu Arg Lys His Ile Ser Asn Ile Phe Leu Ser Asn
145                 150                 155                 160 ggc cta gcc tgg aat aaa gac tca aaa aaa ttt tat ttt atc gac tcc     528
Gly Leu Ala Trp Asn Lys Asp Ser Lys Lys Phe Tyr Phe Ile Asp Ser
                165                 170                 175 aat aaa aga aca ata gat cag ttt gat tat gat tct gaa aat tta att     576
Asn Lys Arg Thr Ile Asp Gln Phe Asp Tyr Asp Ser Glu Asn Leu Ile
            180                 185                 190 ata tca aat tgt caa cca ttg ttt act ctg gac aaa cat ggg ata cag     624
Ile Ser Asn Cys Gln Pro Leu Phe Thr Leu Asp Lys His Gly Ile Gln
        195                 200                 205 ggt tta cct gat gcc caa acg ata gat gaa aat gat aat tta tgg gtt     672
```

|  |  |  |  |  |  |  |  |  |  |  |  |  |  |  |
|---|---|---|---|---|---|---|---|---|---|---|---|---|---|---|
| Gly | Leu | Pro | Asp | Ala | Gln | Thr | Ile | Asp | Glu | Asn | Asp | Asn | Leu | Trp | Val |
| | | 210 | | | | | 215 | | | | 220 | | | | |

| gct | ata | gtt | cga | gga | gga | aaa | gtt | ata | aat | att | ggt | act | aag | caa | ccc | 720 |
|---|---|---|---|---|---|---|---|---|---|---|---|---|---|---|---|---|
| Ala | Ile | Val | Arg | Gly | Gly | Lys | Val | Ile | Asn | Ile | Gly | Thr | Lys | Gln | Pro | |
| 225 | | | | | 230 | | | | | 235 | | | | | 240 | |

| gaa | tct | ttg | ctt | ggt | gtt | att | aac | atg | cct | gaa | agt | ttg | ata | act | tca | 768 |
|---|---|---|---|---|---|---|---|---|---|---|---|---|---|---|---|---|
| Glu | Ser | Leu | Leu | Gly | Val | Ile | Asn | Met | Pro | Glu | Ser | Leu | Ile | Thr | Ser | |
| | | | | 245 | | | | | 250 | | | | | 255 | | |

| gtt | tgt | ttt | gga | gga | tca | aag | ttg | gac | gaa | ctt | tat | gta | acg | act | tct | 816 |
|---|---|---|---|---|---|---|---|---|---|---|---|---|---|---|---|---|
| Val | Cys | Phe | Gly | Gly | Ser | Lys | Leu | Asp | Glu | Leu | Tyr | Val | Thr | Thr | Ser | |
| | | | 260 | | | | | 265 | | | | | 270 | | | |

| ggt | atc | aaa | gag | tat | gaa | act | gac | tct | aca | aaa | cta | gta | aag | ggt | gga | 864 |
|---|---|---|---|---|---|---|---|---|---|---|---|---|---|---|---|---|
| Gly | Ile | Lys | Glu | Tyr | Glu | Thr | Asp | Ser | Thr | Lys | Leu | Val | Lys | Gly | Gly | |
| | | 275 | | | | | 280 | | | | | 285 | | | | |

| ttg | tac | aga | gtt | act | gga | tta | ggt | gtt | aaa | ggt | tta | ccc | gca | cac | aga | 912 |
|---|---|---|---|---|---|---|---|---|---|---|---|---|---|---|---|---|
| Leu | Tyr | Arg | Val | Thr | Gly | Leu | Gly | Val | Lys | Gly | Leu | Pro | Ala | His | Arg | |
| 290 | | | | | 295 | | | | | 300 | | | | | | |

| ttc | agt | ctc | taa | | | | | | | | | | | | | 924 |
|---|---|---|---|---|---|---|---|---|---|---|---|---|---|---|---|---|
| Phe | Ser | Leu | | | | | | | | | | | | | | |
| 305 | | | | | | | | | | | | | | | | |

<210> SEQ ID NO 2
<211> LENGTH: 307
<212> TYPE: PRT
<213> ORGANISM: Luciola lateralis

<400> SEQUENCE: 2

| Met | Ser | Pro | Val | Ile | Glu | Gln | Ile | Thr | Glu | Val | Asp | Asn | Phe | Gln | Ile |
|---|---|---|---|---|---|---|---|---|---|---|---|---|---|---|---|
| 1 | | | | 5 | | | | | 10 | | | | | 15 | |

| Gly | Glu | Gly | Pro | His | Trp | Asp | Thr | Glu | Thr | Gln | Ser | Leu | Tyr | Phe | Val |
|---|---|---|---|---|---|---|---|---|---|---|---|---|---|---|---|
| | | | 20 | | | | | 25 | | | | | 30 | | |

| Asp | Ile | Leu | Glu | Lys | Ser | Ile | His | Lys | Tyr | Val | Pro | Ser | Thr | Lys | Gln |
|---|---|---|---|---|---|---|---|---|---|---|---|---|---|---|---|
| | | | 35 | | | | | 40 | | | | | 45 | | |

| His | Thr | Lys | Met | Ile | Leu | Asn | Lys | Arg | Pro | Ser | Phe | Ile | Ile | Pro | Ile |
|---|---|---|---|---|---|---|---|---|---|---|---|---|---|---|---|
| | 50 | | | | | 55 | | | | | 60 | | | | |

| Lys | Glu | Thr | Ser | Asp | Arg | Phe | Val | Ile | Ser | Leu | Glu | Arg | Asp | Ile | Cys |
|---|---|---|---|---|---|---|---|---|---|---|---|---|---|---|---|
| 65 | | | | | 70 | | | | | 75 | | | | | 80 |

| Val | Leu | Thr | Trp | Asp | Gly | Val | Ser | Ala | Thr | Pro | Ser | His | Leu | Glu | Thr |
|---|---|---|---|---|---|---|---|---|---|---|---|---|---|---|---|
| | | | | 85 | | | | | 90 | | | | | 95 | |

| Ile | Val | Thr | Val | Asp | Thr | Gly | Ile | Glu | Gly | Asn | Thr | Phe | Asn | Asp | Gly |
|---|---|---|---|---|---|---|---|---|---|---|---|---|---|---|---|
| | | | 100 | | | | | 105 | | | | | 110 | | |

| Lys | Ala | Asp | Ala | Phe | Gly | Asn | Leu | Trp | Ala | Gly | Thr | Leu | Tyr | Ser | Lys |
|---|---|---|---|---|---|---|---|---|---|---|---|---|---|---|---|
| | | | 115 | | | | | 120 | | | | | 125 | | |

| Phe | Asp | Ile | Glu | Lys | Gln | Gly | Pro | Asn | Thr | Gly | Thr | Leu | Tyr | Ser | Leu |
|---|---|---|---|---|---|---|---|---|---|---|---|---|---|---|---|
| | 130 | | | | | 135 | | | | | 140 | | | | |

| Ser | Asn | Lys | Gln | Leu | Arg | Lys | His | Ile | Ser | Asn | Ile | Phe | Leu | Ser | Asn |
|---|---|---|---|---|---|---|---|---|---|---|---|---|---|---|---|
| 145 | | | | | 150 | | | | | 155 | | | | | 160 |

| Gly | Leu | Ala | Trp | Asn | Lys | Asp | Ser | Lys | Lys | Phe | Tyr | Phe | Ile | Asp | Ser |
|---|---|---|---|---|---|---|---|---|---|---|---|---|---|---|---|
| | | | | 165 | | | | | 170 | | | | | 175 | |

| Asn | Lys | Arg | Thr | Ile | Asp | Gln | Phe | Asp | Tyr | Asp | Ser | Glu | Asn | Leu | Ile |
|---|---|---|---|---|---|---|---|---|---|---|---|---|---|---|---|
| | | | 180 | | | | | 185 | | | | | 190 | | |

| Ile | Ser | Asn | Cys | Gln | Pro | Leu | Phe | Thr | Leu | Asp | Lys | His | Gly | Ile | Gln |
|---|---|---|---|---|---|---|---|---|---|---|---|---|---|---|---|
| | | | 195 | | | | | 200 | | | | | 205 | | |

| Gly | Leu | Pro | Asp | Ala | Gln | Thr | Ile | Asp | Glu | Asn | Asp | Asn | Leu | Trp | Val |
|---|---|---|---|---|---|---|---|---|---|---|---|---|---|---|---|
| | | 210 | | | | | 215 | | | | 220 | | | | |

| Ala | Ile | Val | Arg | Gly | Gly | Lys | Val | Ile | Asn | Ile | Gly | Thr | Lys | Gln | Pro |
|---|---|---|---|---|---|---|---|---|---|---|---|---|---|---|---|
| 225 | | | | | 230 | | | | | 235 | | | | | 240 |

Glu Ser Leu Leu Gly Val Ile Asn Met Pro Glu Ser Leu Ile Thr Ser
                245                 250                 255

Val Cys Phe Gly Gly Ser Lys Leu Asp Glu Leu Tyr Val Thr Thr Ser
            260                 265                 270

Gly Ile Lys Glu Tyr Glu Thr Asp Ser Thr Lys Leu Val Lys Gly Gly
        275                 280                 285

Leu Tyr Arg Val Thr Gly Leu Gly Val Lys Gly Leu Pro Ala His Arg
    290                 295                 300

Phe Ser Leu
305

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (3)..(3)
<223> OTHER INFORMATION: n is one of g, c, a, or t
<220> FEATURE:
<221> NAME/KEY: misc_feature
<222> LOCATION: (9)..(9)
<223> OTHER INFORMATION: n is one of g, c, a, or t
<220> FEATURE:
<221> NAME/KEY: misc_feature
<222> LOCATION: (12)..(12)
<223> OTHER INFORMATION: n is one of g, c, a, or t

<400> SEQUENCE: 3
ggngarggnc cncaytggga                                              20

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (8)..(8)
<223> OTHER INFORMATION: n is one of g, c, a, or t
<220> FEATURE:
<221> NAME/KEY: misc_feature
<222> LOCATION: (14)..(14)
<223> OTHER INFORMATION: n is one of g, c, a, or t
<220> FEATURE:
<221> NAME/KEY: misc_feature
<222> LOCATION: (20)..(20)
<223> OTHER INFORMATION: n is one of g, c, a, or t

<400> SEQUENCE: 4
crtcdatngt ytgnccrtcn gg                                           22

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
ggacaaacat gggatacagg                                              20

<210> SEQ ID NO 6
<211> LENGTH: 21

```
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
caggctgtac aatgttcctg t                                              21

<210> SEQ ID NO 7
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
gacaaaccga tcagatgttt c                                              21

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
gttgttttgt cgatggtacg                                                20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
cttgggatgg tgttagtgcc                                                20

<210> SEQ ID NO 10
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
taccgttgat acgggaatcg                                                20

<210> SEQ ID NO 11
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
atgtcgccag ttattgaaca g                                              21

<210> SEQ ID NO 12
<211> LENGTH: 21
<212> TYPE: DNA
```

```
<213> ORGANISM: ARTIFICIAL SEQUENCE
<220> FEATURE:
<223> OTHER INFORMATION: SYNTHETIC DNA

<400> SEQUENCE: 12
ttagagactg aatctgtgtg c                                              21
```

GENES ENCODING PROTEINS CAPABLE OF REGENERATING LUCIFERIN, RECOMBINANT DNA AND PROCESS FOR PRODUCING PROTEIN CAPABLE OF REGENERATING LUCIFERIN

TECHNICAL FIELD

The present invention relates to a gene encoding a protein that is capable of regenerating luciferin, a recombinant DNA, and a process for producing a protein capable of regenerating luciferin.

BACKGROUND ART

Luciferin is a substrate of luciferase, a bioluminescence enzyme. After emitting light as a result of luciferase reaction, luciferin is converted into oxyluciferin. ATP measurement methods using luciferase are widely used in the fields of medicine and food hygiene. However, luciferin used as a substrate is expensive and the luciferase reaction is inhibited by oxyluciferin produced after the reaction. Thus, removal of oxyluciferin or regeneration to luciferin is considered to enable further development of the ATP measurement methods: using luciferase. A protein which is derived from a firefly and capable of regenerating luciferin from oxyluciferin has been found (U.S. Pat. No. 5,814,504). However, only a small quantity of the protein can be extracted from a firefly body so that industrial application of this protein has been difficult.

Addition of such a protein capable of regenerating luciferin to the luciferin-luciferase reaction system enables improvement in durability of luminescence and reduction in the amount of luciferase and luciferin to be used.

DISCLOSURE OF THE INVENTION

The object of the present invention is to provide a process for producing a protein capable of regenerating luciferin, using a recombinant DNA producing the protein capable of regenerating luciferin.

As a result of dedicated research on the above object, the present inventors have succeeded in isolating a gene which is derived from Coleoptera and which encodes a protein capable of regenerating luciferin, determining the gene structure of the same, and obtaining a recombinant DNA by inserting a gene encoding a protein capable of regenerating luciferin into a vector DNA. Then, the present inventors have completed the present invention by finding that a protein capable of regenerating luciferin can efficiently be produced by culturing a transformant or a transductant wherein the recombinant DNA is contained in a host cell.

That is, a first invention of the present application is an isolated or synthesized gene which encodes a protein comprising the amino acid sequence represented by SEQ ID NO: 2.

A second invention of the present application is an isolated or synthesized gene which encodes a protein comprising an amino acid sequence comprising a deletion, substitution or addition of one or more amino acids with respect to the amino, acid sequence represented by SEQ ID NO: 2 and being capable of regenerating luciferin.

A third invention of the present application is an isolated or synthesized gene which hybridizes with the complementary strand sequence of a DNA comprising the nucleotide sequence represented by SEQ ID NO: 1 under stringent conditions and encodes a protein capable of regenerating luciferin.

A fourth invention of the present application is a recombinant DNA, which is characterized in that the above-described isolated or synthesized gene is inserted into a vector DNA.

A fifth invention of the present application is a transformant or transductant comprising the above-described recombinant DNA.

A sixth invention of the present application is a process for producing a protein capable of regenerating luciferin, which is characterized in that the process comprises culturing the above-described transformant or transductant in a medium, and collecting therefrom the protein capable of regenerating luciferin.

Hereinafter, the above-described protein capable of regenerating luciferin may at times simply be abbreviated as a "luciferin-regenerating enzyme".

Moreover, a DNA encoding the protein capable of regenerating luciferin or a DNA encoding the protein capable of regenerating luciferin and further comprising a non-translation region, may at times be abbreviated as a "luciferin-regenerating enzyme gene".

THE BEST MODE FOR CARRYING OUT THE INVENTION

Hereinafter, the present invention is described in detail.

The gene of the present invention encoding a protein capable of regenerating luciferin is obtained from Coleoptera having a luciferin-luciferase reaction. The gene encoding a protein capable of regenerating luciferin of the present invention includes all genes which have an activity of regenerating luciferin when those are expressed. Preferred examples of such a gene include a gene encoding the amino acid sequence represented by SEQ ID NO: 2 of the sequence listing, and a gene comprising the nucleotide sequence represented by SEQ ID NO: 1 of the sequence listing. Taking codon degeneracy into consideration, the gene encoding the amino acid sequence represented by SEQ ID NO: 2 of the sequence listing includes various nucleotide sequences. That is to say, the gene encoding the amino acid sequence represented by SEQ ID NO: 2 may be selected from among such various nucleotide sequences, considering various elements of a gene expression system such as a preferred codon based on the type of a host cell and prevention of a higher order structure formed by a transcribed RNA. The selected nucleotide sequence may be either a DNA cloned from the nature or an artificial chemically synthesized DNA.

To obtain the luciferin-regenerating enzyme gene of the present invention, a poly(A)+RNA is first prepared from a Heike firefly by the following method. A method of extracting the total RNA from Coleoptera tissues is not limited as long as the method can efficiently obtain RNA with minimal damage. For example, known methods such as the phenol/SDS method and the guanidine isothiocyanate/cesium chloride method can be applied. Poly(A)+RNA can be separated from the thus obtained total RNA using an oligo(dT) carrier. Otherwise, a kit which obtains poly(A)+RNA without extracting the total RNA may also be used (MPG Direct MRNA Purification Kit, CPG, INC. etc.)

Then, a single stranded cDNA is synthesized with reverse transcriptase, using the poly(A)+RNA as a template and also using oligo(dT) primers, random primers or the like. Thereafter, a double stranded cDNA is synthesized by the Gubler and Hoffman method, the Okayama-Berg method (Molecular Cloning, $2^{nd}$ edition, Cold Spring Harbor Press, 1989) or others. If the expression level of the enzyme gene is low, the cDNA may be amplified by PCR, using a cDNA library preparation kit [Capfinder PCR cDNA Library Construction Kit (CLONTECH) etc.] The thus synthesized cDNA can be cloned into a cloning vector such as a phage vector or plasmid by blunt-ending, adding a linker, adding restriction sites by PCR and others.

The partial sequence of the gene of interest can be obtained by performing PCR (polymerase chain reaction), using the thus obtained cDNA or cDNA library as a template. The sequence used as a primer herein may be based on any part of the amino acid sequence of the luciferin-regenerating enzyme, but it is desired to select a sequence which has fewer codon degeneracy and does not form a complicated higher order structure. Where there is codon degeneracy, mixed primers or primers containing inosine can be used. Whether the amplified product obtained by PCR is a part of a luciferin-regenerating enzyme gene is easily confirmed by analysis of the nucleotide sequence using a 370A DNA sequence system (PerkinElmer). If the amplified product is confirmed to be a part of a luciferin-regenerating enzyme gene, primers are prepared from the sequence, and 5'RACE and 3'RACE (Rapid Amplification of cDNA End: PCR PROTOCOLS A Guide to Methods and Applications, ACADEMIC press INC. p.28–38) are carried out to determine unknown 5'- and 3'-terminal regions. According to the above operations, a full-length luciferin-regenerating enzyme gene is easily sequenced. For 5'RACE and 3'RACE, for example, 5'-Full RACE Core Set (TaKaRa) and 3'-Full RACE Core Set (TaKaRa) can be used.

It is also possible to screen the luciferin-regenerating enzyme gene from a cDNA library by performing hybridization under stringent conditions. A DNA fragment used as a probe can be obtained by PCR, using, as primers, oligonucleotides synthesized on the basis of the amino acid sequence of a luciferin-regenerating enzyme. The obtained DNA fragment can be converted into a probe by labeling. For labeling, various substances such as radioisotope or biotin can be applied, but labeling by the random priming method is desirable. The preparation of a cDNA library can be carried out, for example, using a ZAP Express Vector Kit of STRATAGENE. The labeling of a DNA fragment and the detection of hybridization can be carried out, for example, using a DIG DNA labeling/detection system (Boehringer Mannheim) or the like.

The above-stated "stringent conditions" means conditions where only a specific hybrid is selectively formed and a signal is detected, while a non-specific hybrid is not formed. Although these conditions are different depending on each species of organism, the conditions can easily be determined by analyzing certain properties such as salt concentration or temperature for hybridization and washing process according to standard techniques. As such conditions, hybridization is carried out overnight (approximately 8 to 16 hours) using 5 x SSC, a 1.0% (W/V) nucleic acid blocking reagent for hybridization (Boehringer Mannheim), 0.1% (W/V) N-lauroyl sarcosine and 0.02% (W/V) SDS. For washing, 0.1 x SSC and 0.1 % (W/V) SDS are used, the concentration of SSC is set within the range of 0.1 fold, and the washing is started at a temperature of 37° C. and then increased to 65° C. Under such conditions, a membrane is washed so that a fixed DNA-derived signal can be differentiated from the background, and thereafter the detection of a probe is carried out.

A DNA hybridized under these conditions has a high probability of encoding a polypeptide having a luciferin-regenerating enzyme activity, but it also includes a mutant DNA which might cause the luciferin-regenerating enzyme activity to be lost. However, such a mutant DNA can easily be eliminated by determining, after performing transformation, the ability of the transformant to generate a luciferin-regenerating enzyme activity.

After a luciferin-regenerating enzyme gene is obtained by the above-described method, the gene is incorporated into a vector DNA by standard techniques. Examples of a vector DNA used herein include a plasmid DNA such as pUC19 (Takara Shuzo), pBR322 (Takara Shuzo), pT7Blue (Novagen), pBluescript SK+(Stratagene) and pMAL-C2 (NEW England Labs), a bacteriophage DNA such as λ ENBL3 (Stratagene) and A DASH II (Funakoshi), and others. The obtained recombinant DNA is transformed or transduced into, for example, *Escherichia coli* K-12, preferably *Escherichia coli* JM109 (Toyobo), DH5a (Toyobo) or XL1-Blue (Funakoshi), thereby obtaining a transformant or transductant, respectively. In addition to the above, examples of a host cell used herein include bacteria such as *Escherichia coli* other than *E. coli* K-12, yeast, mold, Actinomycetes, silk worms, animal cells and others.

Transformation can be carried out by, for example, D. M. Morrison's method (Method in Enzymology, 68, 326–331, 1979). Transduction can be carried out by, for example, B. Hohn's method (Method in Enzymology, 68, 299–309, 1979).

A purified recombinant DNA can be obtained from the above transformant or transductant by, for example, P. Guerry et al.'s method [J. Bacteriology, vol. 116, 1064–1066 (1973)] and D. B. Clewell's method [J. Bacteriology, vol. 110, 667–676 (1972)].

Further, the entire nucleotide sequence of the gene encoding a protein capable of regenerating luciferin is analyzed (see SEQ ID NO: 1) using a DNA comprising the above luciferin-regenerating enzyme gene and a 370A DNA sequence system (PerkinElmer) indicated in the later described Example 1, Item (9). Then, the primary sequence of the amino acids of a polypeptide translated by a gene comprising the above nucleotide sequence, is determined (see SEQ ID NO: 2).

The present invention encompasses any gene which encodes a protein comprising an amino acid sequence comprising a deletion, substitution or addition of one or more, preferably several amino acids with respect to the amino acid sequence represented by SEQ ID NO: 2, and being capable of regenerating luciferin.

Moreover, the present invention encompasses any gene which encodes a protein having a 60% or more, preferably 80% or more homology with the amino acid sequence of SEQ ID NO: 2 and being capable of regenerating luciferin.

Any method can be employed to obtain a gene which encodes a protein comprising an amino acid sequence comprising a deletion, substitution or addition of one or more amino acids with respect to the amino acid sequence represented by SEQ ID NO: 2, and being capable of regenerating luciferin. Examples of such a method include site-directed mutagenesis which is a known technique to cause point mutation or deletion to occur in a gene, a method which involves selectively cleaving a gene, removing or adding a selected nucleotide and ligating the gene, and an oligonucleotide mutation induction method.

Using a transformant or transductant capable of regenerating luciferin obtained as described above, for example, a strain belonging to the genus *Escherichia,* a protein capable of regenerating luciferin can be produced as described below. The above microorganism may be cultured by any normal solid culture method, but it is preferably cultured by a liquid culture method.

A medium used for culturing the above microorganism is supplemented with, for example, one or more types of nitrogen source such as yeast extract, Peptone, meat extract, corn steep liquor, or exudates of soybean or wheat koji, and one or more types of inorganic salt such as potassium dihydrogenphosphate, dipotassium hydrogenphosphate, magnesium sulfate, ferric chloride, ferric sulfate or manganese sulfate, and if necessary, this medium is appropriately supplemented with carbohydrate material, vitamin and the like.

The initial pH of a medium is appropriately adjusted to 7 to 9. Preferably, culture is performed at 30° C. to 42° C., preferably at around 37° C. for 6 to 24 hours by aeration agitation-submerged culture, shaking culture, stationary culture or the like. After culturing, the protein capable of regenerating luciferin can be collected from the culture product by normal techniques for collecting enzymes.

Cells are isolated from the culture product by an operation such as filtration or centrifugation and are then washed. A luciferin-regenerating enzyme is preferably collected from these cells. In this case, intact cells can directly be used, but preferably, the luciferin-regenerating enzyme is collected from the cells by, for example, a method which disrupts cells using various disruptive means such as an ultrasonicator, French press or Dynamill, a method which digests cell walls using a cell wall digesting enzyme such as lysozyme, and a method which extracts the enzyme from the cells using a surfactant such as Triton X-100.

The luciferin-regenerating enzyme can be isolated from the thus obtained crude cell homogenization solution containing the enzyme by any standard enzyme purification technique. Preferably performed is an appropriate combination of such techniques including ammonium sulfate salting out technique, precipitation technique using organic solvents, ion exchange chromatography, gel filtration chromatography, adsorption chromatography and electrophoresis.

The ability of the enzyme to regenerate luciferin can be measured by the following method.

(Method for measuring ability to regenerate luciferin)
(Reagent)
A 0.1 mM oxyluciferin
B 0.01 mM D-cysteine
C 25 mM glycylglycine +5.4mM magnesium sulfate
D 10 mM ATP (pH7.8)
E 5 mg/ml luciferase
(Procedure)
1. Prepare a mixed solution of the following reagents.
0.005 ml A
0.010 ml B
0.085 ml C
2. Add 0.01 ml of a protein solution and allow to react at 37C for a certain time.
3. Mix 0.01 ml of the reaction solution with 0.1 ml of C.
4. Prepare a luciferase mixed solution of the following reagents.
10 ml D
1 ml E
5. Add 0.1 ml of the mixed solution of 4 to that of 3, and then measure the amount of light emitted using a luminometer.

EXAMPLES

Hereinafter, the present invention is described further in detail by Examples.

Example 1.

(1) Preparation of Heike firefly mRNA

The tail portion of Heike firefly (10 g), disrupted with a mortar and pestle, was suspended in 10 ml of ISOGEN (Wako Pure Chemical Industries, Ltd.), a reagent for extracting RNA, and then centrifuged at 2700 r.p.m. for 5 min, thereby obtaining an RNA fraction. From the fraction, 0.5 mg of Poly(A)+RNA was obtained according to the method described in Current Protocols in Molecular Biology (WILEY Interscience, 1989).

(2) Synthesis of primers

Primers were prepared on the basis of a Heike firefly-derived luciferin-regenerating enzyme (U.S. Pat. No. 5814504, Example 3) which was separately obtained by the present inventors. Initially, a Heike firefly-derived luciferin-regenerating enzyme was fragmentized with peptidase and the obtained product was subjected to reversed-phase partition chromatography to obtain a peak. Using an ABI470A protein sequencer (PerkinElmer), the amino acid sequences of the obtained several types of peptides were determined. Based on the thus determined amino acid sequences, primers of HR12 (SEQ ID NO: 4) and KN14 (SEQ ID NO: 3) were designed, and synthesis was carried out by the custom DNA synthesis service of Amersham Pharmacia Biotech.

(3) RT-PCR

A reaction solution was prepared to have the following composition, and a reverse transcription reaction was allowed to proceed at 42° C. for 30 minutes. Thereafter, denaturation was performed at 99° C. for 5 minutes, and the obtained reaction product was then stored at 5° C.

| (Composition of reaction solution) | Amount used |
| --- | --- |
| 25 mM MgCl$_2$ | 4 µl |
| *10xRNA PCR buffer | 2 µl |
| 10 mM dNTP Mixture | 2 µl |
| 40 U/µl RNase Inhibitor | 0.5 µl |
| 5 U/µl *AMV reverse transcriptase XL | 1 µl |
| 2.5 pmol/µl *oligo dT-Adaptor primer | 1 µl |
| mRNA | 1 µg |
| Sterile distilled water | add water to a final volume of 20 µl |

*manufactured by Takara Shuzo

Thereafter, 80 µl of the reaction solution prepared to have the following composition was added to a tube in which reverse transcription had been performed. Then,: PCR was performed for 30 cycles under the following reaction conditions: denaturation at 94° C. for 30 seconds, annealing at 62° C. for 30 seconds, and elongation reaction at 72° C. for 1.5 minutes.

| (Composition of reaction solution) | Amount used |
| --- | --- |
| 20 pmol/µl primer KN14 (SEQ ID NO: 3) | 1 µl |
| 20 pmol/µl primer GC3 (SEQ ID NO: 4) | 1 µl |
| *10xRNA PCR buffer | 8 µl |
| 25 mM MgCl$_2$ | 6 µl |
| 5 U/µl *Taq polymerase | 0.5 µl |
| Sterile distilled water | 63.5 µl |

*manufactured by Takara Shuzo

After completion of PCR, the reaction solution was subjected to agarose gel electrophoresis, so that a band in a position of approximately 600 bp regarded as a target amplified fragment was confirmed. The band was cut out and purified with GENECLEAN II (BIO 101).

(4) The nucleotide sequence of the purified DNA fragment was determined and analyzed using a 370A DNA sequence system (PerkinElmer). Thus, an amino acid sequence which had been deduced from the determined nucleotide sequence was confirmed to comprise the peptide fragment obtained in (2).

(5) Analysis of downstream region by 3'RACE

First, a primer was designed according to the above analysis for DNA sequence, and then synthesized by the synthesis service of Amersham Pharmacia Biotech (HN003, SEQ ID NO: 5). 3' RACE was performed using the primer, the above mRNA and a 3'-Full RACE CoreSet (Takara Shuzo), thereby amplifying unknown 3' regions. The reaction solution was subjected to agarose electrophoresis, from which a DNA fragment of approximately 400 bp was purified and extracted with RecoChip (Takara Shuzo), and the nucleotide sequence was determined and analyzed using a DNA sequencer. Thus, the 5' region of the determined nucleotide sequence was confirmed to contain a sequence being the same as that of the above gene encoding a protein capable of regenerating luciferin.

(6) Analysis of upstream region by 5' RACE

First, primers were designed according to the above analysis for DNA sequence, and then synthesized by the synthesis service of Amersham Pharmacia Biotech [HR101 (SEQ ID NO: 6), HR102 (SEQ ID NO: 7), HR103 (SEQ ID NO: 8), HN104 (SEQ ID NO: 9) and HN105 (SEQ ID NO: 10)]. RT-PCR was performed using the primers, the above Heike firefly mRNA and a 5'-Full RACE CoreSet (Takara Shuzo), thereby amplifying unknown 5' regions. The reaction solution was subjected to agarose electrophoresis, a DNA fragment of approximately 300 bp was purified with RecoChip (Takara Shuzo), and the nucleotide sequence was determined and analyzed using a DNA sequencer. Thus, the 3' region of the determined nucleotide sequence was confirmed to contain a sequence being the same as that of the above gene encoding a protein capable of regenerating luciferin.

(7) Recovery of gene fragment by RT-PCR

A translation initiation codon and a termination codon were deduced from the above three nucleotide sequences, and then the primer DNAs of the nucleotide sequences corresponding to the N-terminal region and the C-terminal region were synthesized by the synthesis service of Amersham Pharmacia Biotech [porf101 (SEQ ID NO: 11), porf102 (SEQ ID NO: 12)]. RT-PCR was performed using these primers and the above Heike firefly mRNA, and then the reaction solution was analyzed by agarose electrophoresis. As a result, a band of approximately 900 bp was confirmed. A DNA fragment contained in the band was purified with RecoChip (Takara Shuzo). The purified DNA fragment was cloned into a plasmid pT7Blue (Novagen), and *Escherichia coli* JM109 was then transformed with the obtained plasmid. The obtained transformant strain, *Escherichia coli* JM109 (pHlre), was deposited with the National Institute of Advanced Industrial Science and Technology, an Independent Administrative Institution under the Ministry of Economy, Trade and Industry, AIST Tsukuba (Central 6, Higashi 1-1-1, Tsukuba, Ibaraki, Japan) under accession No. FERM BP-7248 on Jul. 27, 2000.

(8) Confirmation of activity

*E. coli* JM109 (pHlre) cells were shake-cultured to 100 Kletts at 37° C. in 10 ml of a TY medium (1% bacto trypton, 0.5% bactoyeast extract, 0.5% NaCl, pH 7.0) containing 75 µg/ml ampicillin. Then, IPTG was added to reach a final concentration of 1 mM, followed by another 4 hours of culture. The culture solution was treated 4 times (20 seconds each) using an ultrasonicator (Ultrasonicgenerator, Nissei) while being cooled on ice. The solution was placed into an Eppendorf tube, and centrifuged at 12,000 r.p.m. with a micro centrifuge for 10 minutes, thereby separating the supernatant from the precipitation fractions. The supernatant was transferred to another Eppendorf tube, and the ability to regenerate luciferin was measured by the previously described method for measuring enzyme activity. While *E. coli* comprising vectors only had 0.95 kcount/ml, *E. coli* JM109 (phlre) had 11.0 kcount/ml and was confirmed to be capable of regenerating luciferin.

(9) Analysis of gene encoding protein capable of regenerating luciferin

Confirmation of the luciferin-regenerating ability of *E. coli* JM109 (pHlre) revealed that the inserted pHlre fragments comprised a luciferin-regenerating enzyme gene. Then, the nucleotide sequence was determined for this plasmid DNA using a 370A DNA sequence system (PerkinElmer). The determined nucleotide sequence and an amino acid sequence which is considered to be translated from the DNA sequence are shown in SEQ ID NO: 1 and SEQ ID NO: 2, respectively. The luciferin-regenerating enzyme gene had a coding region of 924 bp and encoded 307 amino acids.

Example 2.

Plaque hybridization

The cDNA library of a Heike firefly was prepared by using a ZAP Express Vector Kit (STRATAGENE). Then, using the amplified fragment of approximately 600 bp obtained by RT-PCR in Example 1 (3) as a template and HR12 (SEQ ID NO: 4) and KN14 (SEQ ID NO: 3) as primers, a digoxigenin (DIG)-labeled DNA probe was prepared by PCR.

Sterile distilled water (37.75 µl), 5 µl of 10 x buffer, 2 types of 1 µl of 100 pmol/µl primer DNA solution, 1 µl of template DNA solution, 4 µl of 10 x PCR DIG Mix (Boehringer Mannheim) and 0.25 µl of ExTaq DNA polymerase were placed into a 0.2 ml volume tube for PCR, these solutions were mixed, 20 µl of mineral oil was dropped therein, and the mixture was set to a RoboCycler Gradient 96. PCR program was set at (1) 95° C., 30 seconds, (2) 95° C., 30 seconds, (3) 62° C., 30 seconds, (4) 72° C., 40 seconds and (5) 72° C., 2 minutes, and a PCR reaction was carried out such that operations (2) to (4) were repeated for 45 cycles followed by (5) 72° C., 2 minutes. An amplified fragment was collected from the reaction solution by ethanol precipitation, and the fragment was dissolved in 50 µl of TE buffer so as to obtain a DIG-labeled probe.

Using the thus prepared Heike firefly cDNA library and DNA probe, plaque hybridization was carried out. According to the manual attached to the kit, approximately 5×10³ plaques were formed on each of five agar mediums. Thereafter, DNA was transferred from the plaques on these mediums to a HyBond-N+nylon transfer membrane (Amersham) according to the manual attached to the membrane kit. This time, to exclude non-specific signals, DNA was transferred from a single agar medium to two membranes.

Hybridization and detection were carried out on the above-described membranes using the prepared DIG-DNA probe and DIG system (Boehringer Mannheim) according to the descriptions on pages 37 to 40 of "User guide for performing hybridization using DIG system", Boehringer Mannheim, (1996).

In this screening, 4 strains were obtained as positive clone candidate strains. The obtained candidate strains were subjected to the second screening, which was similar to the above screening so as to obtain one purified positive clone strain.

In vitro excision to collect a plasmid pHP was carried out on this phage clone according to the manual attached to the kit.

*Escherichia coli* JM109 was transformed with the plasmid pHP, and a plasmid DNA was prepared from the obtained transformant and was used as a sample for analyzing the nucleotide sequence. The nucleotide sequence of an inserted cDNA was analyzed by the previously known method of using a Taq DyeDeoxy Terminator Cycle Sequencing Kit (PerkinElmer). As a result, it was confirmed that the inserted cDNA had a nucleotide sequence identical to SEQ ID NO:

1 of the sequence listing and is a gene encoding a luciferin-regenerating enzyme derived from a Heike firefly.

INDUSTRIAL APPLICABILITY

The present invention is industrially very useful because the invention enables efficient production of a protein capable of regenerating luciferin.

This specification includes part or all of the contents as disclosed in the specification of Japanese Patent Application No. 2000-228227, which is a priority document of the present application. All publications, patents and patent applications cited herein are incorporated herein by reference in their entirety.

What is claimed is:

1. An isolated or synthesized DNA molecule, which encodes a protein comprising the amino acid sequence represented by SEQ ID NO: 2.

2. A recombinant vector comprising the isolated or synthesized DNA molecule according to claim 1.

3. A host cell transformed or transduced with the recombinant vector according to claim 2.

4. A process for producing a protein capable of regenerating luciferin, which comprises:
   culturing the host cell according to claim 3 in a medium and
   isolating the protein capable of regenerating luciferin.

5. An isolated or synthesized DNA molecule, which hybridizes with the complementary strand sequence of a DNA comprising the nucleotide sequence represented by SEQ ID NO: 1 under stringent conditions and
   which encodes a protein capable of regenerating luciferin,
   wherein the stringent conditions comprise a hybridization carried out overnight using 5x SSC, a 1.0% (w/v) nucleic acid blocking reagent 0.1% (w/v) N-lauroyl sarcosine and 0.02% (w/v) SDS, and a wash using 0.1x SSC and 0.1% (w/v) SDS at 37° C. then at 65° C.

6. A recombinant vector comprising the isolated or synthesized DNA molecule according to claim 5.

7. A host cell transformed or transduced with the vector according to claim 6.

8. A process for producing a protein capable of regenerating luciferin, which comprises:
   culturing the host cell according to claim 7 in a medium and
   isolating the protein capable of regenerating luciferin.

9. The host cell of claim 7, which is a bacterium.

10. The host cell of claim 7, which is a yeast or mold.

11. The host cell of claim 7, which is an animal cell.

12. The host cell of claim 7, wherein said DNA molecule comprises codons preferred by said host cell.

* * * * *

UNITED STATES PATENT AND TRADEMARK OFFICE
CERTIFICATE OF CORRECTION

PATENT NO. : 7,101,694 B2 Page 1 of 1
APPLICATION NO. : 10/333740
DATED : September 5, 2006
INVENTOR(S) : Hirokawa et al.

It is certified that error appears in the above-identified patent and that said Letters Patent is hereby corrected as shown below:

On the title page, Item (54) and Column 1, the Title information is incorrect. Item (54) and Column 1 should read:

-- (54) GENE ENCODING PROTEIN CAPABLE OF REGENERATING LUCIFERIN, RECOMBINANT DNA AND PROCESS FOR PRODUCING PROTEIN CAPABLE OF REGENERATING LUCIFERIN --

Signed and Sealed this

Fifth Day of December, 2006

JON W. DUDAS
*Director of the United States Patent and Trademark Office*